United States Patent
Tenn, III et al.

(10) Patent No.: US 9,834,506 B2
(45) Date of Patent: Dec. 5, 2017

(54) HETEROGENEOUS HYDROCYANATION

(71) Applicant: INVISTA NORTH AMERICA S.A R.L., Wilmington, DE (US)

(72) Inventors: William J. Tenn, III, Beaumont, TX (US); Sudkir N. V. K. Aki, Katy, TX (US)

(73) Assignee: INVISTA NORTH AMERICA S.A.R.L., Wilmington, DE (US)

(*) Notice: Subject to any disclaimer, the term of this patent is extended or adjusted under 35 U.S.C. 154(b) by 0 days.

(21) Appl. No.: 15/102,792

(22) PCT Filed: Dec. 18, 2014

(86) PCT No.: PCT/US2014/071274
§ 371 (c)(1),
(2) Date: Jun. 8, 2016

(87) PCT Pub. No.: WO2015/095594
PCT Pub. Date: Jun. 25, 2015

(65) Prior Publication Data
US 2016/0311763 A1     Oct. 27, 2016

Related U.S. Application Data

(60) Provisional application No. 61/918,152, filed on Dec. 19, 2013.

(51) Int. Cl.
| | | |
|---|---|---|
| C07C 255/22 | (2006.01) | |
| C07C 253/10 | (2006.01) | |
| B01J 21/06 | (2006.01) | |
| B01J 23/02 | (2006.01) | |
| B01J 23/04 | (2006.01) | |
| B01J 23/06 | (2006.01) | |
| B01J 23/10 | (2006.01) | |
| B01J 27/236 | (2006.01) | |
| B01J 27/26 | (2006.01) | |
| B01J 31/06 | (2006.01) | |

(52) U.S. Cl.
CPC ........... *C07C 255/22* (2013.01); *B01J 21/066* (2013.01); *B01J 23/02* (2013.01); *B01J 23/04* (2013.01); *B01J 23/06* (2013.01); *B01J 23/10* (2013.01); *B01J 27/236* (2013.01); *B01J 27/26* (2013.01); *B01J 31/06* (2013.01); *C07C 253/10* (2013.01)

(58) Field of Classification Search
CPC .................................................. C07C 255/22
See application file for complete search history.

(56) References Cited

U.S. PATENT DOCUMENTS

| | | | |
|---|---|---|---|
| 2,904,581 | A | 9/1959 | Coraor et al. |
| 3,526,654 | A | 9/1970 | Hildebrand |
| 4,367,179 | A | 1/1983 | Pesa et al. |
| 7,371,884 | B2 | 5/2008 | Oevering et al. |
| 8,394,981 | B2 | 3/2013 | Garner et al. |
| 2006/0194979 | A1 | 8/2006 | Bartsch |

FOREIGN PATENT DOCUMENTS

WO    2015/095594 A2    6/2015

OTHER PUBLICATIONS

International Search Report and Written Opinion Received for PCT Application No. PCT/US2014/071274, dated Jun. 12, 2015, 8 pages.
International Preliminary Report and Patentability Report Received for PCT Patent Application No. PCT/US2014/071274, dated Jun. 30, 2016, 7 pages.
Misra, Chanakaya, "Industrial Alumina Chemicals", American Chemical Society, vol. 59, Issue 10, 1986, pp. 706A-706A.
Sasoi; "Puralox/Catalox® High Purity Activated Aluminas", online available at <http://www.sasoltechdata.com/tds/PURALOX_CATALOX.pdf); 2005, 9 pages.

*Primary Examiner* — Shawquia Jackson
(74) *Attorney, Agent, or Firm* — Robert B. Furr, Jr.; Dennis P Santini

(57) ABSTRACT

The present invention relates to an improved process for addition of hydrogen cyanide across olefins and, in particular, to the use of a specific aluminum oxide to catalyze the reaction. The aluminum oxide catalyst must have total alkali metal and/or alkaline earth metal content, measured in the form of alkali metal oxide and/or alkaline earth metal oxide, of less than 3,000 ppm by weight.

18 Claims, No Drawings

HETEROGENEOUS HYDROCYANATION

FIELD OF THE INVENTION

The present invention relates to an improved process for addition of hydrogen cyanide (HCN) across olefins and, in particular, to the use of a specific aluminum oxide to catalyze the reaction.

BACKGROUND OF THE INVENTION

Commercial processes for producing adiponitrile, an important intermediate in the manufacture of nylon-6,6 and related products, typically include a stage in which 3-pentenenitrile (3PN) or 4-pentenenitrile (4PN) is hydrocyanated in the presence of nickel (0) catalyst to form adiponitrile. It is known that cis-2-pentenenitrile (c2PN) is formed as a byproduct during such a hydrocyanation. The formation of c2PN represents an adiponitrile yield loss in the process. Furthermore, the accumulation of c2PN during the hydrocyanation reaction is undesirable because it behaves as a catalyst poison. However, the removal of c2PN is not straightforward. It can be separated from unreacted 3PN by distillation. Alternatively, it can be removed by reaction with an alkali metal sulfite and bisulfite solution but this can complicate the procedure. With this in mind, rather than physically removing the c2PN, efforts have focused on converting it to a useful product. In this regard, it may be isomerized to 3PN, which can then be recycled back into the hydrocyanation reaction.

The isomerization of c2PN to 3PN has been described in U.S. Pat. No. 3,526,654 and U.S. Patent Publication No. 2006/0194979. Both describe that the isomerization reaction may be carried out in the presence of aluminum oxide catalyst. In U.S. Pat. No. 3,526,654, the catalyst is disclosed to be weakly basic solid state material selected from the class consisting of silica gel, alumina, and sodium-calcium aluminosilicate, with Alcoa F-1 aluminum oxide exemplified; while in U.S. Patent Publication No. 2006/0194979, the aluminum oxide catalyst has a BET surface area at least 50 m$^2$/g.

Catalysts known for the Markovnikov addition of HCN to activated olefins tend to polymerize the activated olefin and the HCN as well. Other catalysts capable of the Markovnikov addition of HCN to olefins are not effective for non-activated olefins such as 3PN and 2-methyl-3-butenenitrile (2M3BN), which do not have an activating group in the alpha-position. U.S. Pat. No. 2,904,581 discloses that addition of HCN across activated olefins can be accomplished using tetracyanonickelate (II) salts as catalyst. However, conversions are low (less than 15%) when the olefin is α,β-disubstituted. U.S. Pat. No. 4,367,179 discloses that supported Group IA, and Group IIA metals are effective catalysts for the addition of RCN to activated olefins to yield the Markovnikov addition products. However, the highly basic nature of the supported alkali and alkaline earth metal catalysts necessitates that they be used in a vapor phase process to avoid the problem of polymerization of both the HCN and the activated olefin.

U.S. Pat. No. 7,371,884 discloses that certain amines are useful as homogeneous catalysts for the Markovnikov addition of HCN to acrylonitrile to produce succinonitrile. However, a separation process for separating the catalyst from the reaction product is required after the reaction.

U.S. Pat. No. 8,394,981 discloses that certain homogenous biphosphite nickel complexes are useful as catalysts for the conversion of c2PN to greater than 90% adiponitrile, with minor formation of ethylsuccinonitrile (ESN).

None of the above publications teach a process for addition of HCN across olefins in the liquid or vapor phase, and, in particular, to the use of the specific aluminum oxide required for the present process to catalyze such a reaction. A simple, economical, improved process for addition of HCN across olefins in liquid or vapor phase hydrocyanation is provided by the present invention.

SUMMARY OF THE INVENTION

The present invention provides an improved process for addition of HCN across olefins, activated or not, at reaction conditions, in the presence of a specific aluminum oxide catalyst, more particularly describe hereinafter.

An embodiment of the present invention, therefore, provides an improved process for addition of HCN across olefins which comprises contacting an olefin with hydrogen cyanide at reaction conditions in the presence of an aluminum oxide catalyst, wherein the aluminum oxide catalyst has total alkali metal and/or alkaline earth metal content, measured in the form of alkali metal oxide and/or alkaline earth metal oxide, of less than 3,000 ppm by weight total.

Another embodiment of the present invention, therefore, provides an improved process for addition of HCN across olefins which comprises contacting an olefin with hydrogen cyanide at reaction conditions in the presence of an aluminum oxide catalyst, wherein the aluminum oxide catalyst has total alkali metal and/or alkaline earth metal content, measured in the form of alkali metal oxide and/or alkaline earth metal oxide, for example, sodium, potassium, and/or calcium, measured in the form of metal oxide, of less than 1000 ppm by weight.

Another embodiment of the present invention, therefore, provides an improved process for addition of HCN across olefins which comprises contacting an olefin with hydrogen cyanide at reaction conditions in the presence of an aluminum oxide catalyst, wherein the aluminum oxide catalyst has total alkali metal and/or alkaline earth metal content, measured in the form of alkali metal oxide and/or alkaline earth metal oxide, for example, sodium, potassium, and/or calcium, measured in the form of metal oxide, of from 0 to 100 ppm, for example, from less than 25 to 100 ppm by weight.

Another embodiment of the present invention, therefore, provides an improved process for addition of HCN across olefins which comprises contacting an olefin with hydrogen cyanide at reaction conditions including a temperature of from 50 to 450° C. and pressure from 760 to 5,000 mmHg in the presence of an aluminum oxide catalyst, wherein the aluminum oxide catalyst has total alkali metal and/or alkaline earth metal content, measured in the form of alkali metal oxide and/or alkaline earth metal oxide, for example, sodium, potassium, and/or calcium, measured in the form of metal oxide, of less than 3,000 ppm by weight total.

Another embodiment of the present invention, therefore, provides an improved process for manufacturing ESN which comprises contacting c2PN, 3PN or a combination thereof with hydrogen cyanide at reaction conditions including a temperature of from 50 to 450° C. and pressure from 760 to 5,000 mmHg in the presence of an aluminum oxide catalyst, wherein the aluminum oxide catalyst has total alkali metal and/or alkaline earth metal content, measured in the form of alkali metal oxide and/or alkaline earth metal oxide, of less than 3,000 ppm by weight.

Another embodiment of the present invention, therefore, provides an improved process for manufacturing DMSN which comprises contacting 2M2BN, 2M3BN or a combination thereof with hydrogen cyanide at reaction conditions including a temperature of from 50 to 450° C. and pressure from 760 to 5,000 mmHg in the presence of an aluminum oxide catalyst, wherein the aluminum oxide catalyst has total alkali metal and/or alkaline earth metal content, measured in the form of alkali metal oxide and/or alkaline earth metal oxide, of less than 3,000 ppm by weight.

DETAILED DESCRIPTION OF THE INVENTION

As a result of intense research in view of the above, we have discovered an improved process for addition of HCN across olefins in the liquid or vapor phase, and, in particular, to the use of the specific aluminum oxide required for the present process to catalyze such a reaction. The substantially pure aluminum oxide (e.g. total alkali metal and/or alkaline earth metal content, measured in the form of alkali metal oxide and/or alkaline earth metal oxide, of less than 3000 ppm, such as less than 1000 ppm, for example from 0 to 100 ppm by weight) used as catalyst is found to be an effective heterogeneous catalyst for the Markovnikov addition of HCN across olefins, activated or not, in this process. No polymerization of HCN is observed in the reaction solution (minimal HCN polymerization may be observed on the surface of the catalyst), and no polymerization of the activated olefin is observed. Further, the catalyst can be readily separated from the reaction product. Additionally, the catalyst is capable of converting both 2M3BN and 2-methyl-2-butenenitrile (2M2BN) to dimethylsuccinonitrile (DMSN), and both 3PN and 2-pentenenitrile to 2-ethylsuccinonitrile (ESN). Other traditional basic catalyst systems would not be effective for hydrocyanation of 3PN, or 2M3BN, which do not have an activating group alpha to the olefin. However, the catalyst for use herein is capable of isomerizing the unreactive 3PN or 2M3BN to the active 2-pentenenitrile or 2M2BN, respectively, in the present process.

The improved process of the invention comprises contacting an olefin with hydrogen cyanide at reaction conditions including a temperature of from 50 to 450° C. and pressure from 760 to 5,000 mmHg in the presence of an aluminum oxide catalyst, wherein the aluminum oxide catalyst has total alkali metal and/or alkaline earth metal content, measured in the form of alkali metal oxide and/or alkaline earth metal oxide, of less than 3,000 ppm by weight total.

The term "activated olefin", as used herein, unless otherwise indicated, means an olefin that has an electron-withdrawing group in the alpha position. Activated olefins for use as reactant in the present process include 2-pentenenitrile, and 2-methyl-2-butenenitrile. Non-limiting examples of activated olefins for use herein are selected from the group consisting of cis-2-pentenenitrile, 2-methyl-2-pentenenitrile, and combinations thereof.

The term "ESN", as used herein, unless otherwise indicated, means ethylsuccinonitrie. ESN is a product of the present process when the olefin is c2PN or 3PN. The term "DMSN", as used herein, unless otherwise indicated, means dimethylsuccinonitrile, e.g. 2,3-dimethylsuccinonitrile. DMSN is a product of the present process when the olefin is 2M2BN, e.g. cis-2-methyl-2-butenenitrile or trans-2-methyl-2-butenenitrile, or 2M3BN.

The hydrogen cyanide (HCN), also known as hydrocyanic acid, prussic acid or formonitrile, used as a reactant in the process of this invention can be any of those commercially available. Typically, HCN can be manufactured by catalytically reacting ammonia and air with methane or natural gas.

The catalyst for use in the present invention is substantially pure aluminum oxide with total alkali metal and/or alkaline earth metal content, measured in the form of alkali metal oxide and/or alkaline earth metal oxide, of less than 3,000 ppm by weight, such as less than 1000 ppm by weight, such as from 0 to 100 ppm, for example from less than 25 ppm to 100 ppm by weight. The catalyst is capable of converting both 3PN and 2M3BN (which are not activated olefins) to 2-pentenenitrile and 2M2BN, respectively, via isomerization. This enables hydrocyanation. Other traditional basic catalyst systems would not be effective for hydrocyanation of 3PN, or 2M3BN, which do not have an activating group alpha to the olefin. A non-limiting example of a commercially available aluminum oxide for use as catalyst in the present process is gamma-alumina Catalox® SCFa-140 having a $Na_2O$ content of 5.5 ppm.

Catalysts for use in the present invention are commercially available. Examples of suitable aluminum oxide catalysts for use in the process include AL-3995, AL-3996 and AL-4126, which are commercially available from Engelhard; and Catalox SCFa-140 and Catalox SBa-200, which are commercially available from Sasol. Suitable aluminum oxide catalysts may be prepared using the techniques described in the "Puralox/Catalox® High Purity activated aluminas" Sasol product brochure (http://www.sasoltechdata.com/tds/PURALOX_CATALOX.pdf), wherein aluminum alkoxide is used to produce synthetic boehmite of high purity.

Standard analytical techniques for determining metal content typically measure the content of alkali metal and/or alkaline earth metal impurities as the corresponding alkali metal and/or alkaline earth metal oxide. Hence, the alkali metal and/or alkaline earth metal contents of the aluminum oxide catalyst used in the present process are as measured in the form of the corresponding alkali metal oxide and/or alkaline earth metal oxide. For example, where the alkali metal is sodium, the sodium content is measured as $Na_2O$. Examples of techniques which may be used to determine the alkali metal and/or alkaline earth metal contents of the catalyst used in the present process include atomic absorption and flame photometry methods, such as described in Industrial Alumina Chemicals, ACS Monograph 184, Chanakaya Misra, American Chemical Society, 1986.

The catalyst is present in the process in a catalytically effective amount, which in the usual case means a concentration of from 5% to 50% by weight of the reaction mixture of HCN and olefin, preferably from 10% to 40%, even more preferably from 20% to 30%.

The catalyst for use in the present process can be in the form of powders or as shaped bodies, for example in the form of beads, cylindrical extrudates, spheres, rings, spirals, chopped film or granules.

The present invention process may be conducted in the liquid or vapor phase at reaction conditions including a temperature of from 50 to 450° C. and pressure from 760 to 5,000 mmHg. In the liquid phase, reaction conditions include a temperature from 50 to 150° C., such as from 55 to 125° C., for example from 65 to 100° C. In either batch or continuous mode, the process is run in the liquid phase at pressure from 760 to 5,000 mmHg, such as from 760 to 2,500 mmHg, for example from 1,500 to 2,500 mmHg. In the vapor phase, reaction conditions include a temperature from >150 to 450° C., such as from 160 to 225° C., for example from 170 to 200° C. In either a packed bed configuration or in a fluidized bed mode, the process is run in the vapor phase at pressure from 760 to 5,000 mmHg, for example from 760 to 3,500 mmHg.

The process of the invention may be carried out in any reactor which is capable of containing a liquid or vapor medium and may be batch mode or continuous. When run continuously, the process is preferably conducted in a continuously stirred tank reactor, with continuous stirring and with continuous addition of reactants and continuous removal of product. Alternatively, the process can be run in a fixed-bed reactor, or bubble column. The process may be carried out in a reactor capable of containing a liquid or vapor feed with the catalyst in a packed bed.

In any suitable reactor, it is preferable to adjust the temperature in the reaction zone, the concentration of reactants in the reaction zone, and the flow rate of the reactants into and products out of the reaction zone so that from 25 to 100% by weight, preferably from 75 to 100% by weight, of the HCN is converted on each pass through the reactor. With proper adjustment of concentrations of reactants in the feed stream, of flow rates and of temperature, the residence time of the reactants in a continuous reactor can be, for example, from 5 minutes to 24 hours, such as from 30 minutes to 16 hours, for example from 1 to 4 hours.

Residence time (e.g. in minutes) is determined by measuring the volume (e.g. in milliliters) of the reaction zone and then dividing this figure by the flow rate (e.g. in milliliters per minute) of the reactants through the reactor. The time required for the present improved process to provide a given conversion of HCN depends upon the conditions under which it is run. Time will therefore vary with temperature, pressure, concentrations of reactants and catalyst; and like factors. Generally, however, in a continuous mode, the process is run to give a residence time from 5 minutes to 24 hours, such as from 30 minutes to 16 hours, for example from 0.5 to 8 hours. In the batch mode, the residence time is ordinarily from 1 to 4 hours.

On completion of the reaction, the catalyst can be separated from the reaction mixture/product by filtration, decantation or centrifugation, and reused. If the process is run in a continuous fashion, the catalyst can simply be allowed to remain in the reactor while fresh reactants are fed in and product is removed.

The following Examples demonstrate the present invention and its capability for use. The invention is capable of other and different embodiments, and its several details are capable of modifications in various apparent respects, without departing from the spirit and scope of the present invention. Accordingly, the Examples are to be regarded as illustrative in nature and non-limiting. All parts and percentages are by weight unless otherwise indicated.

EXAMPLES

Example 1

To a 50 mL jacketed glass laboratory extractor (reactor), equipped with a magnetic stir bar, digital stir plate, and maintained at 100° C. and 760 mmHg, was charged 3 grams of aluminum oxide catalyst (Catalox SCFa-140, product of Sasol) having an $Na_2O$ content of 5.5 ppm. The reactor was purged with flowing nitrogen for 30 minutes. Then 8 mL of refined c2PN was added to the reactor. To the reactor 0.3 mL of adiponitrile (ADN) was added for use as an internal standard. The reactor was then agitated at 700 rpm, and flow of HCN (10% in valeronitrile) to the reactor at 0.5 mL per hour was initiated. After 4 hours, the reactor was allowed to cool to room temperature, and any residual HCN was removed from the reactor with flowing nitrogen. Samples were obtained from the reactor, and product analysis was conducted by gas chromatography.

Example 2

Example 1 was repeated, except that 3PN was the olefin evaluated.

Example 3

Example 1 was repeated, except that magnesium oxide was used as the catalyst.

Example 4

Example 3 was repeated, except that 3PN was the olefin evaluated.

Example 5

Example 1 was repeated, except that 2M3BN was the olefin evaluated.

Example 6

Example 1 was repeated, except that the temperature was maintained at 65° C. during the reaction.

Example 7

Example 6 was repeated, except that aluminum oxide (F-200, product of BASF) having a $Na_2O$ content of 3,000 ppm was used as the catalyst.

Example 8

Example 3 was repeated, except that the temperature was maintained at 65° C. during the reaction.

Example 9

Example 6 was repeated, except that zinc oxide was used as the catalyst.

Example 10

Example 6 was repeated, except that Amberlyst A-26 (product of Dow) was used as the catalyst.

Example 11

Example 6 was repeated, except that nickel (II) cyanide tetrahydrate was used as the catalyst.

Example 12

Example 6 was repeated, except that nickel (II) cyanide was used as the catalyst.

Example 13

Example 6 was repeated, except that monoclinic zirconium oxide was used as the catalyst. The zirconium oxide was subjected to thermal treatment at 200° C. for 16 hours prior to use.

Example 14

Example 13 was repeated, except that the monoclinic zirconium oxide was used directly as the catalyst without any thermal treatment prior to use.

Example 15

Example 6 was repeated, except that tetragonal zirconium oxide was used as the catalyst. The zirconium oxide was subjected to thermal treatment at 200° C. for 16 hours prior to use.

Example 16

Example 15 was repeated, except that the tetragonal zirconium oxide was used directly as the catalyst without any thermal treatment prior to use.

Example 17

Example 6 was repeated, except that lanthanum oxide doped zirconium oxide was used as the catalyst.

Example 18

Example 6 was repeated, except that hydrotalcite (product of SigmaAldrich) was used as the catalyst.

Example 19

Example 18 was repeated, except that the hydrotalcite used as the catalyst was calcined at 600° C. for 4 hours prior to use.

Example 20

Example 6 was repeated, except that 1,3-cyclohexadiene was the olefin evaluated.

Example 21

Example 6 was repeated, except that 1,3-hexadiene was the olefin evaluated.

The results of Examples 1 through 21 are shown in Table 1 below.

TABLE 1

| Ex | Catalyst | Olefin | Temp (° C.) | Product | Yield (%)† |
|---|---|---|---|---|---|
| 1 | SCFa‡ | c2PN | 100 | ESN | 89 |
| 2 | SCFa‡ | 3PN | 100 | ESN | 31 |
| 3 | MgO$^a$ | c2PN | 100 | ESN | 58$^c$ |
| 4 | MgO$^a$ | 3PN | 100 | ESN | 66$^c$ |
| 5 | SCFa‡ | 2M3BN | 100 | DMSN | 15 |
| 6 | SCFa‡ | c2PN | 65 | ESN | 50 |
| 7 | F-200 | c2PN | 65 | ESN | 47$^g$ |
| 8 | MgO$^b$ | c2PN | 65 | ESN | 30$^d$ |
| 9 | ZnO | c2PN | 65 | N/A | 0 |
| 10 | Amberlyst A-26 | c2PN | 65 | ESN | 19$^g$ |
| 11 | Ni(CN)$_2$(H$_2$O)$_4$ | c2PN | 65 | N/A | 0 |
| 12 | [Ni(CN)$_2$]$_n$ | c2PN | 65 | N/A | 0 |
| 13 | mZrO$_2$$^h$ | c2PN | 65 | ESN | 2 |
| 14 | mZrO$_2$$^i$ | c2PN | 65 | ESN | 1 |
| 15 | tZrO$_2$$^i$ | c2PN | 65 | ESN | 1 |
| 16 | tZrO$_2$$^h$ | c2PN | 65 | ESN | 6 |
| 17 | La$_2$O$_3$/ZrO$_2$ | c2PN | 65 | ESN | 46 |
| 18 | Hydrotalcite$^e$ | c2PN | 65 | ESN | 6 |
| 19 | 5MgO/MgAl$_2$O$_4$$^f$ | c2PN | 65 | ESN | 39$^c$ |
| 20 | SCFa‡ | 1,3-cyclohexadiene | 65 | N/A | 0 |
| 21 | SCFa‡ | 1,3-hexadiene | 65 | N/A | 0 |

†Yield based on HCN.
‡SCFa = Catalox SCFa-140 gamma-alumina supplied by Sasol
F-200 = F-200 gamma-alumina supplied by BASF
c2PN = cis-2-pentenenitrile
3PN = cis- and trans-3-pentenenitrile, mixture of isomers
2M3BN = 2-methyl-3-butenenitrile
$^a$MgO (lot 2)
$^b$MgO (lot 1)
$^c$Extensive isomerization and oligomerization
$^d$No isomerization or oligomerization
$^e$Mg$_6$Al$_2$(CO$_3$)(OH)$_{16}$·4(H$_2$O)
$^f$Calcined hydrotalcite (600° C./4 h)
$^g$Some olefin oligomerization
$^h$16 h/200° C.
$^i$No thermal treatment The data presented in Table 1 show the effectiveness of various catalysts on the yield of nitriles produced from the addition of HCN to various olefins. The data show that highly basic catalysts display low yields of nitrile product formation, and formation of oligomers and polymers derived from the olefin and HCN is a significant issue. Likewise, Examples 6 and 7 were performed to assess the impact of alkali metal and/or alkaline earth metal, e.g. sodium, content on the catalyst performance. The Na$_2$O content of Catalox SCFa-140 is 5.5 ppm, and the Na$_2$O content of F-200 is 3,000 ppm. Use of the higher Na$_2$O content catalyst under the same conditions reduced yield by 3% and lead to oligomerization of the olefin. Comparison of Examples 20 and 21 with Example 6 shows that aluminum oxide is not effective for addition of HCN to non-activated olefins. Examples 2, 4 and 5 shows that the catalyst systems are effective even for non-activated olefins (ie. 3PN and 2M3BN) that typically will not undergo hydrocyanation using traditional basic catalysts.

Example 22

For this experiment, a continuous fixed bed reactor was used for the vapor phase hydrocyanation of a 2PN/3PN mixture and 2M2BN. A 1" OD stainless steel reactor equipped with multipoint thermocouple was used. Pure HCN was delivered by means of an ISCO syringe pump and organic liquids were delivered to the reactor using an Eldex metering pump. The reactor was maintained at the desired temperature by means of a band heater. The pressure was controlled by means of a pressure control valve and the reaction product was sampled at regular frequency using a sampling valve. Product was collected in a product tank and the reactor effluent lines were heated to 150° C. to prevent condensation of the product. An on-line gas chromatograph was used to monitor HCN leakage. Samples were analyzed for the reactants (2PN, 3PN and 2M2BN) and products.

The activity of alumina catalyst for hydrocyanation of 2PN/3PN mixture (45/55 2PN/3PN) was studied in this continuous fixed bed reactor. A 55 gram quantity of SCFa-140 alumina was used. Reaction temperature was varied between 170 and 190° C. without any significant catalyst deactivation and the reaction pressure was maintained at 1285 mm Hg. HCN flow rate was varied between 0.7 mL/hour and 2.5 mL/hour and 3PN flow rate was fixed at 0.2 mL/minute. The experiment was run for 190 hours. Isomerization of 3PN to c2PN increased the overall yield to ESN.

Additional losses of 2PN towards the formation of oligomers were observed (~15%). GC-MS analysis indicated the presence of oligomers of c2PN and some hydrocyanation products of the oligomers. Approximately 2 liters of product was generated. Overall conversion of HCN based on ESN formed was 80%. The experimental conditions and results of Example 22 are shown in Table 2 below. In Table 2, "A" is run time in hours; "B" is reaction temperature in ° C.; "C" is reaction pressure in mmHg; "D" is HCN flow rate in mL/hour; "E" is 2PN+3PN conversion %; "F" is 3PN conversion %; "G" is ESN yield; "H" is c2PN conversion based on ESN produced; and "I" is HCN conversion based on ESN produced.

TABLE 2

| A | B | C | D | E | F | G | H | I |
|---|---|---|---|---|---|---|---|---|
| 16 | 170 | 1285 | 0.7 | -1.4 | 62.1 | 0.0 | 0 | -0.1 |
| 19 | 170 | 1285 | 0.8 | 15.7 | 61.4 | 2.4 | 11 | 17.3 |
| 22 | 170 | 1285 | 0.8 | 20.8 | 62.7 | 4.5 | 21 | 32.2 |
| 24 | 170 | 1230 | 2.5 | 18.0 | 61.8 | 4.3 | 20 | 18.6 |
| 40 | 172 | 1285 | 2.5 | 14.6 | 61.1 | 5.7 | 26 | 12.5 |
| 43 | 170 | 1285 | 2.5 | 35.9 | 67.3 | 18.1 | 83 | 39.7 |
| 46 | 170 | 1285 | 2.3 | 42.4 | 68.8 | 24.9 | 114 | 59.7 |
| 48 | 170 | 1285 | 2.5 | 44.7 | 69.9 | 26.7 | 123 | 58.8 |
| 111 | 171 | 1285 | 2.5 | 56.3 | 73.3 | 34.9 | 161 | 76.2 |
| 114 | 170 | 1285 | 2.5 | 56.8 | 73.7 | 36.0 | 165 | 79.0 |
| 117 | 171 | 1285 | 2.5 | 57.9 | 73.3 | 36.5 | 168 | 77.9 |
| 120 | 170 | 1285 | 2.5 | 59.2 | 74.3 | 38 | 175 | 83.5 |
| 135 | 170 | 1285 | 2.5 | 57.0 | 70.7 | 36.6 | 168 | 80.0 |
| 138 | 170 | 1285 | 2.5 | 55.1 | 69.5 | 35.6 | 164 | 77.8 |
| 141 | 180 | 1285 | 2.4 | 55.0 | 71.0 | 35.9 | 165 | 80.1 |
| 144 | 179 | 1285 | 2.5 | 58.5 | 75.6 | 37.5 | 172 | 80.9 |
| 160 | 190 | 1336 | 2.5 | 53.1 | 73.6 | 33.8 | 155 | 73.9 |
| 163 | 190 | 1230 | 2.5 | 51.3 | 72.3 | 32.6 | 150 | 70.3 |
| 166 | 190 | 1285 | 2.5 | 56.5 | 74.8 | 36.1 | 166 | 77.8 |
| 168 | 190 | 1285 | 2.4 | 58.2 | 75.4 | 37.2 | 171 | 83.7 |
| 183 | 190 | 1285 | 2.5 | 55.1 | 73.5 | 34.9 | 160 | 76.3 |

In Table 2, 3PN conversion=(3PN in feed−3PN in product)/3PN in feed; 2PN+3PN conversion=((2PN in feed+3PN in feed)−(2PN in product+3PN in product))/(2PN in feed+3PN in feed); HCN conversion based on ESN produced=(molar flow of ESN in product−molar flow ESN in feed)/molar flow of HCN in feed; ESN yield=(molar flow of ESN in product−molar flow ESN in feed)/(molar flow of 3PN in feed+molar flow of 2PN in feed); and c2PN conversion based on ESN=(molar flow of ESN in product−molar flow ESN in feed)/molar flow of 2PN in feed.

Example 23

In this experiment, the continuous fixed be reactor described in Example 22 was used for the vapor phase hydrocyanation of 2M2BN. In this experiment, 55 grams of SCFa-140 alumina was used as the catalyst. HCN flow rate was fixed at 0.75 mL/hour and the 2M2BN flow rate was maintained at 0.2 mL/minute. The reaction temperature was maintained at 170° C. and the reactor pressure at 1285 mmHg. Overall conversion of HCN under these conditions was found to be 70% with the corresponding conversion of 2M2BN at 5%, providing a yield of DMSN of 5%.

While the illustrative embodiments of the invention have been described with particularity, it will be understood that various other modifications will be apparent to and may be readily made by those skilled in the art without departing from the spirit and scope of the invention. Accordingly, it is not intended that the scope of the claims hereof be limited to the examples and descriptions set forth herein but rather that the claims be construed as encompassing all the features of patentable novelty which reside in the present invention, including all features which would be treated as equivalents thereof by those skilled in the art to which the invention pertains.

What is claimed is:

1. A process for addition of hydrogen cyanide across an olefin which comprises contacting an olefin with hydrogen cyanide at reaction conditions in the presence of an aluminum oxide catalyst, wherein the aluminum oxide catalyst has total alkali metal and/or alkaline earth metal content, measured in the form of alkali metal oxide and/or alkaline earth metal oxide, of less than 3,000 ppm by weight.

2. The process of claim 1 wherein the aluminum oxide catalyst has total alkali metal and/or alkaline earth metal content, measured in the form of alkali metal oxide and/or alkaline earth metal oxide, of less than 1000 ppm by weight.

3. The process of claim 1 wherein the aluminum oxide catalyst has total alkali metal and/or alkaline earth metal content, measured in the form of alkali metal oxide and/or alkaline earth metal oxide, of from 0 to 100 ppm by weight.

4. The process of claim 1 wherein the alkali metal is selected from the group consisting of sodium, potassium and combinations thereof, and the alkaline earth metal is selected from the group consisting of magnesium, calcium and combinations thereof.

5. The process of claim 3 wherein the alkali metal is sodium and the alkaline earth metal is calcium.

6. The process of claim 1 wherein the olefin comprises a pentenenitrile, a butenenitrile or a combination thereof.

7. The process of claim 6 wherein the olefin is selected from the group consisting of cis-2-pentenenitrile, 3-pentenenitrile, 2-methyl-3-butenenitrile, and combinations thereof.

8. The process of claim 3 wherein the olefin is selected from the group consisting of cis-2-pentenenitrile, 3-pentenenitrile, 2-methyl-3-butenenitrile, and combinations thereof.

9. The process of claim 5 wherein the olefin is selected from the group consisting of cis-2-pentenenitrile, 3-pentenenitrile, 2-methyl-3-butenenitrile, and combinations thereof.

10. The process of claim 1 wherein the reaction conditions include a temperature of from 50 to 450° C. and pressure from 760 to 5,000 mmHg.

11. The process of claim 1 wherein the reaction conditions include a temperature of from 50 to 150° C. and pressure from 760 to 5,000 mmHg.

12. The process of claim 1 wherein the reaction conditions include a temperature of from >150 to 450° C. and pressure from 760 to 5,000 mmHg.

13. A process for manufacturing ethylsuccinonitrile which comprises contacting cis-2-pentenenitrile, 3-pentenenitrile or a combination thereof with hydrogen cyanide in the liquid phase or vapor phase at reaction conditions in the presence of an aluminum oxide catalyst, wherein the aluminum oxide catalyst has total alkali metal and/or alkaline earth metal content, measured in the form of alkali metal oxide and/or alkaline earth metal oxide, of less than 3,000 ppm by weight.

14. The process of claim 13 wherein the aluminum oxide catalyst has total alkali metal and/or alkaline earth metal content, measured in the form of alkali metal oxide and/or alkaline earth metal oxide, of less than 1000 ppm by weight.

15. The process of claim 13 wherein the reaction conditions include a temperature of from 55 to 125° C. and pressure from 760 to 2,500 mmHg.

16. The process of claim 13 wherein the reaction conditions include a temperature of from 160 to 225° C. and pressure from 760 to 3,500 mmHg.

17. A process for manufacturing 2,3-dimethylsuccinonitrile which comprises contacting cis-2-methyl-2-butenenitrile, trans-2-methyl-2-butenenitrile, 2-methyl-3-butenenitrile or a combination thereof with hydrogen cyanide in the liquid phase at reaction conditions in the presence of an aluminum oxide catalyst, wherein the aluminum oxide catalyst has total alkali metal and/or alkaline earth metal content, measured in the form of alkali metal oxide and/or alkaline earth metal oxide, of less than 3,000 ppm by weight.

18. The process of claim 17 wherein the aluminum oxide catalyst has total alkali metal and/or alkaline earth metal content, measured in the form of alkali metal oxide and/or alkaline earth metal oxide, of less than 1000 ppm by weight.

* * * * *